United States Patent [19]

Babow et al.

[11] Patent Number: 5,030,108
[45] Date of Patent: Jul. 9, 1991

[54] CARD EDGE BUS BAR ASSEMBLY FOR POWER DISTRIBUTION SYSTEM

[75] Inventors: David A. Babow, Scottsdale; Glenn E. Bennett, Glendale; John E. Lucius, Glendale; Roger N. Polk, Glendale; Frederick H. Rider, Glendale; David S. Szczesny, Glendale, all of Ariz.

[73] Assignee: AMP Incorporated, Harrisburg, Pa.

[21] Appl. No.: 548,133

[22] Filed: Jun. 29, 1990

[51] Int. Cl.⁵ .................................... H05K 1/14
[52] U.S. Cl. .................................... 439/64; 174/72 B; 361/415; 439/108; 439/157; 439/251
[58] Field of Search .................................... 439/59-62, 439/64, 92, 101, 108, 157, 251; 361/407, 413, 415; 174/72 B

[56] References Cited

U.S. PATENT DOCUMENTS

| | | | |
|---|---|---|---|
| 3,708,610 | 1/1973 | Kozel et al. | 174/72 B |
| 4,186,982 | 2/1980 | Cobaugh et al. | 339/17 C |
| 4,381,423 | 4/1983 | Taylor | 174/72 B |
| 4,401,843 | 8/1983 | Harper et al. | 174/72 B |
| 4,755,145 | 7/1988 | Johnson et al. | 439/101 |
| 4,789,352 | 12/1988 | Kreinberg et al. | 439/260 |
| 4,834,665 | 5/1989 | Kreinberg et al. | 439/260 |
| 4,845,589 | 7/1989 | Weidler et al. | 361/342 |
| 4,846,699 | 7/1989 | Glover et al. | 439/64 |
| 4,869,673 | 9/1989 | Kreinberg et al. | 439/64 |
| 4,895,425 | 1/1990 | Iwano et al. | 350/96.20 |
| 4,932,906 | 6/1990 | Kaly et al. | 439/857 |

OTHER PUBLICATIONS

The Western Electrical Engineer, Jan. 1979, "Printed Circuit Board Bus Bars", Strede, pp. 19-23.
Electronics, Jun. 1984, "Bus Bars for PCB Applications Keyed to Design Performance", Parks, pp. 23-26.

Primary Examiner—Neil Abrams
Attorney, Agent, or Firm—Anton P. Ness

[57] ABSTRACT

A bus bar assembly (110) includes a pair of source and return bus bars (118,116) mounted on at least one of the side edges (108,112) of a daughter card (102) and electrically connected by arrays of terminals (172) to power circuits of the card, for use in a system for distributing electrical power to the daughter card module (100) upon insertion into a card cage (10). The pair of bus bars (118,116) is insulated by a cover (120) having a rail (126) for following the guide channels (18,20) of the card cage at each card location. Rearward ends of the bus bars have blades (122,124) which are received into receptacle contacts (46,44) mounted in the card cage above and below the backplane (14), which are mounted at each card location and electrically connected to source and return busses (68,58) of the card cage, with the receptacle contacts (46,44) preferably being float mounted to be easily incrementally moved upon blade receipt during card module (100) insertion.

14 Claims, 11 Drawing Sheets

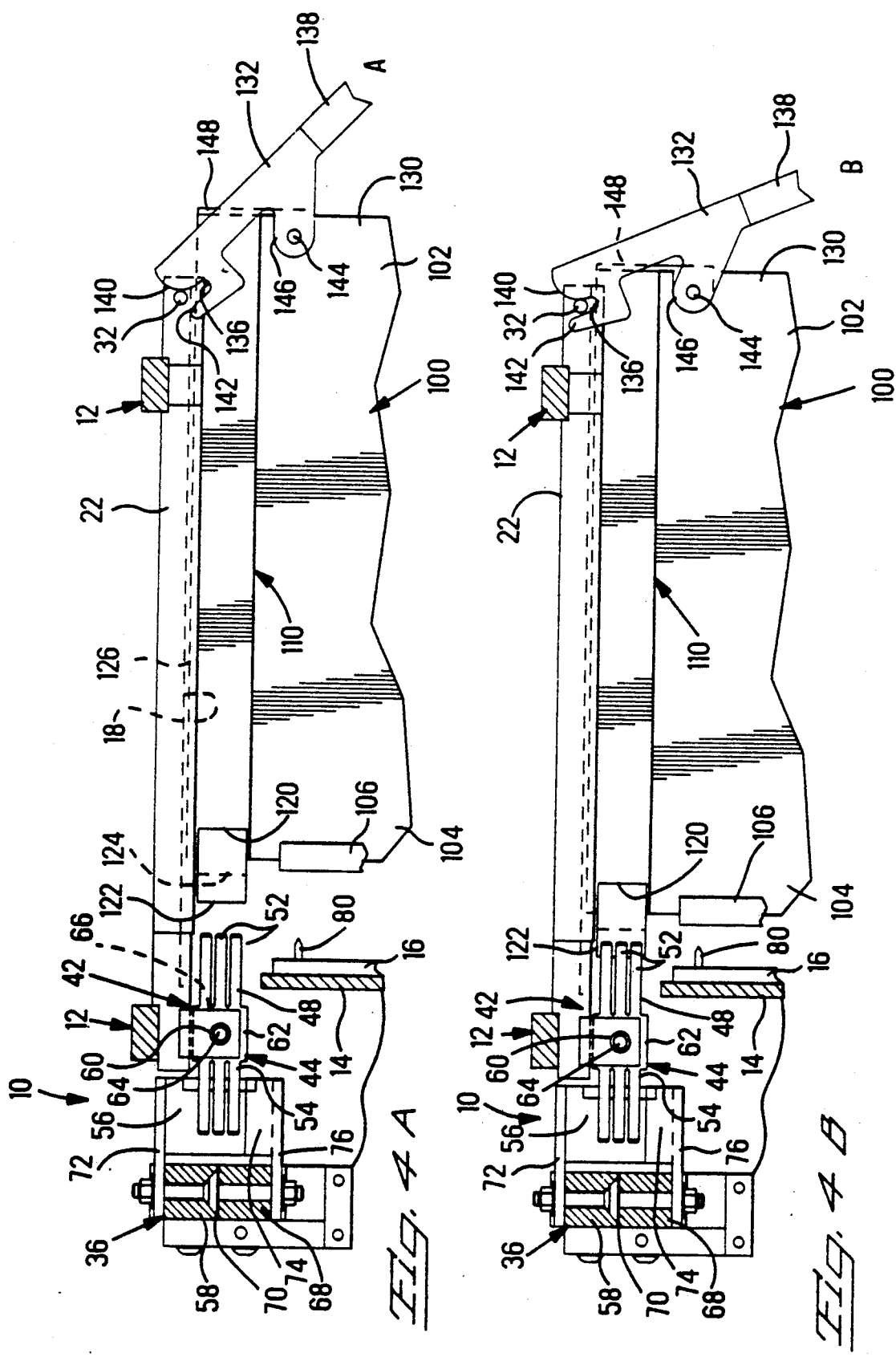

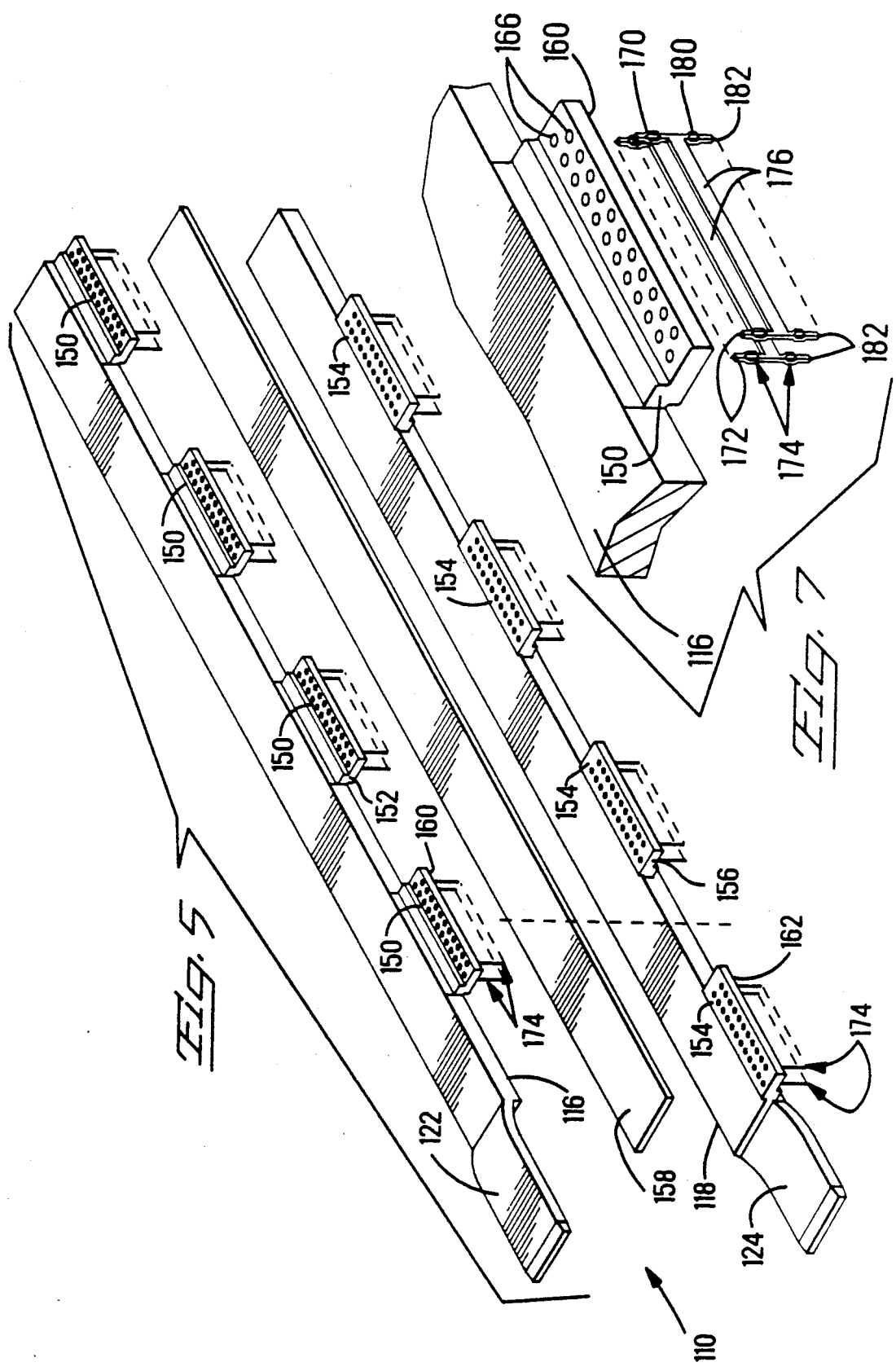

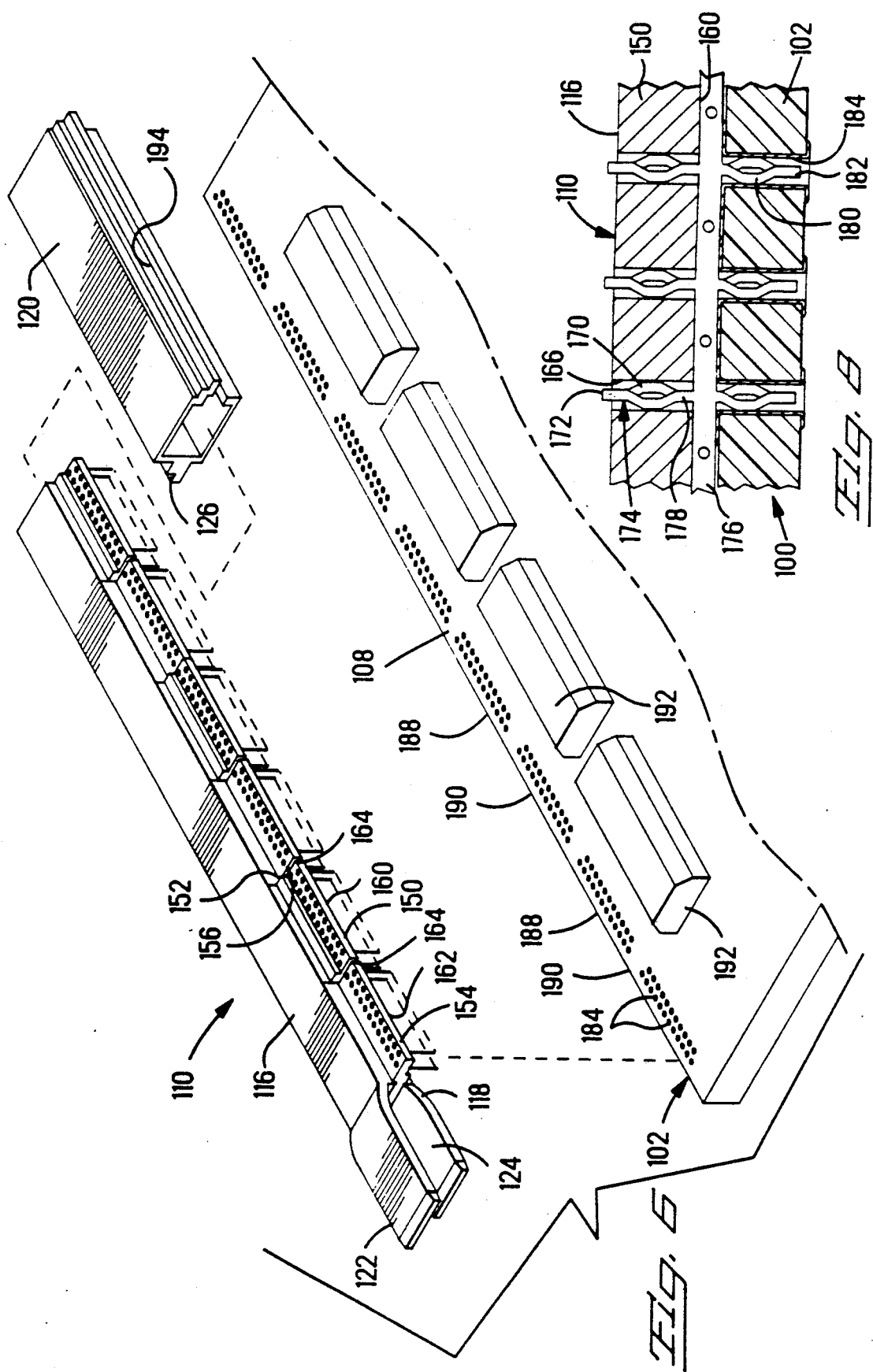

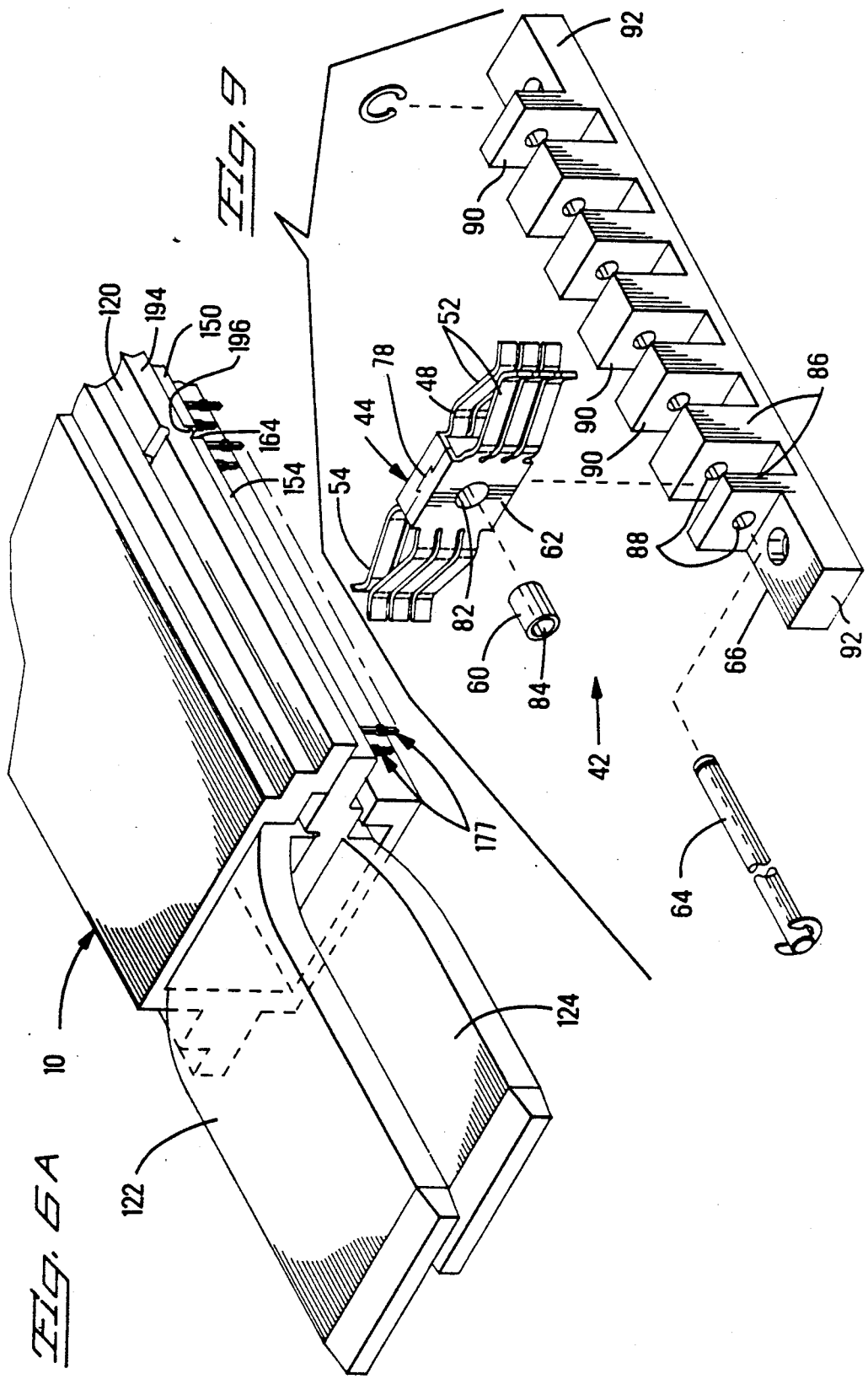

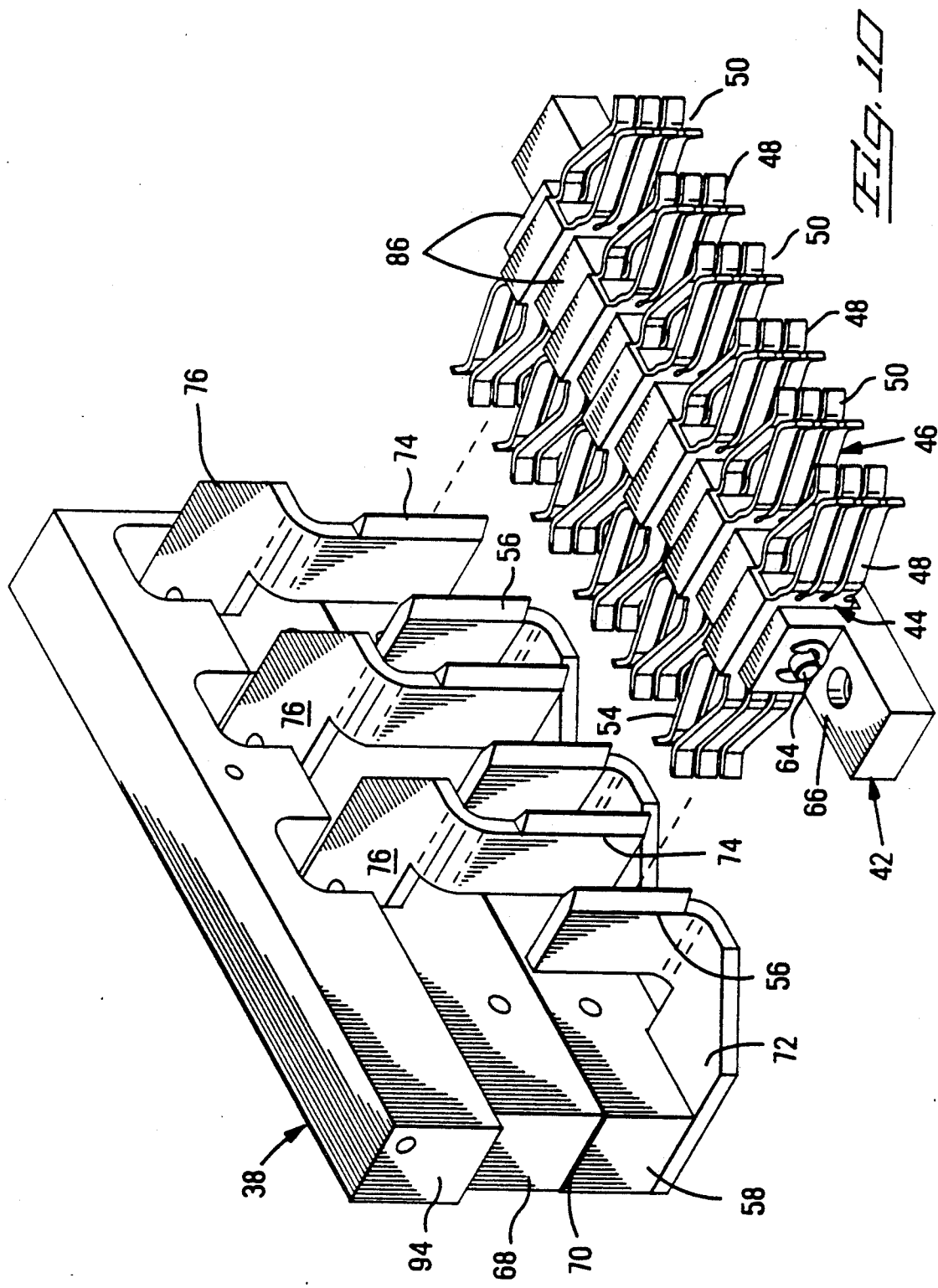

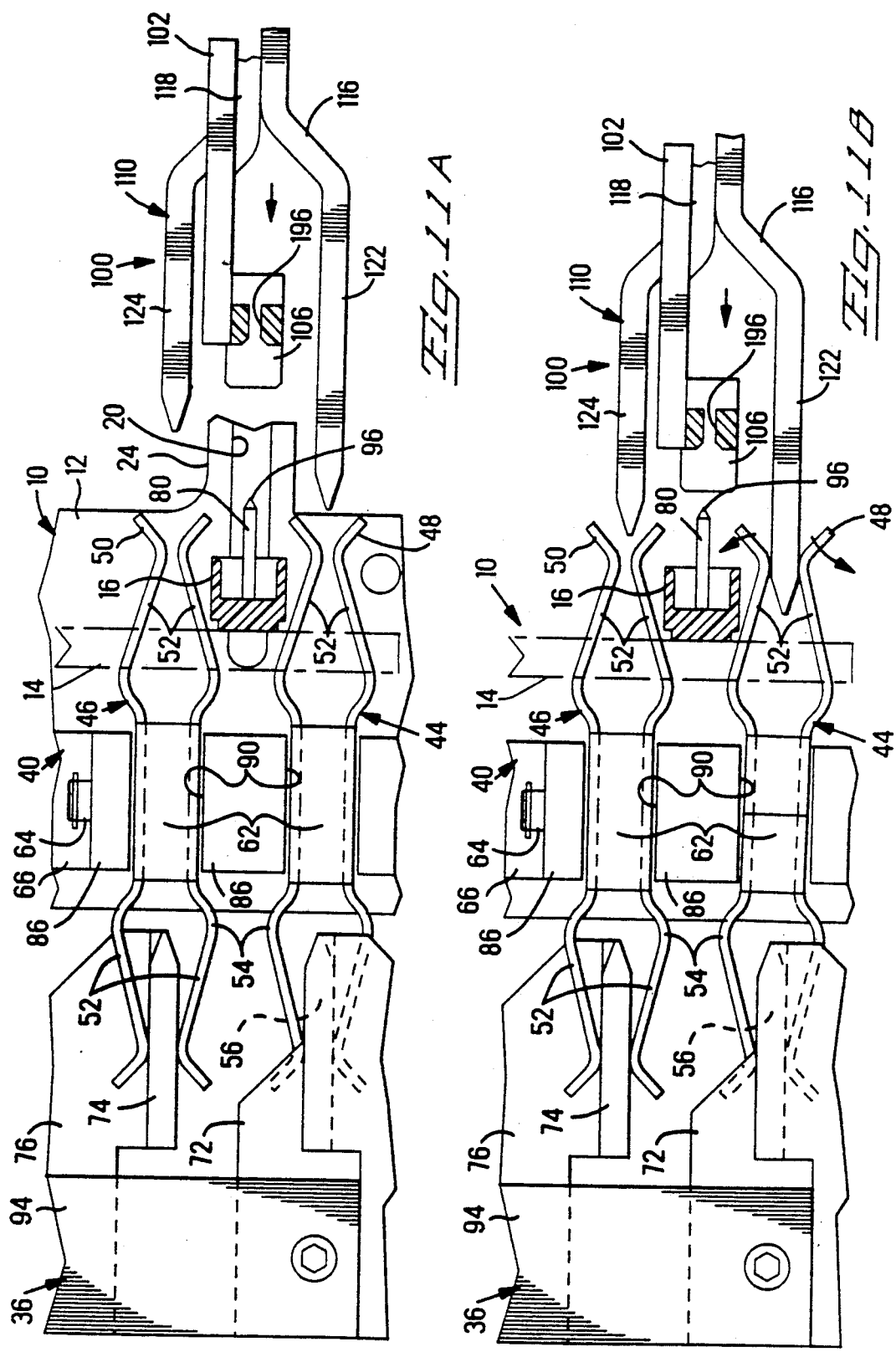

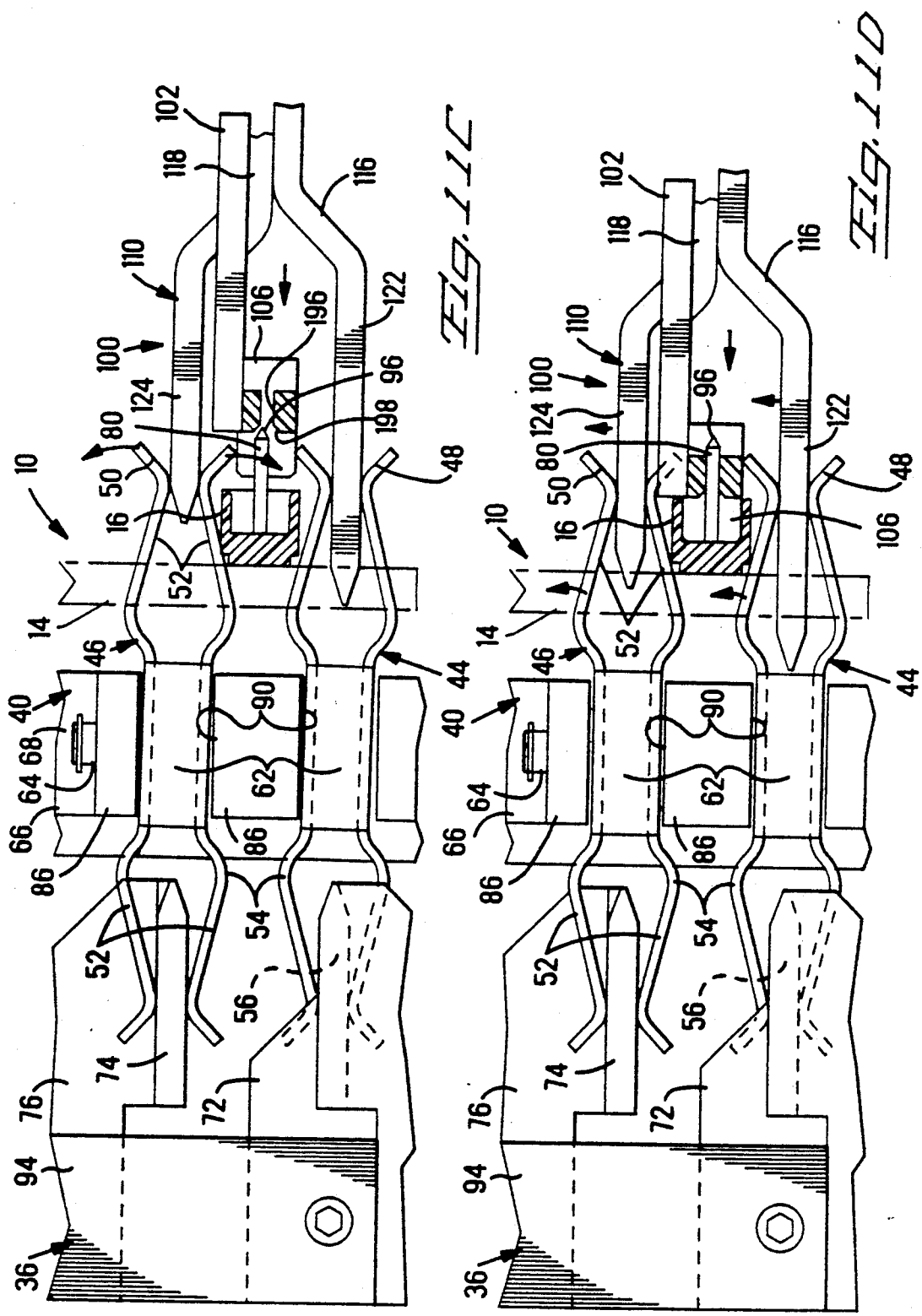

CARD EDGE BUS BAR ASSEMBLY FOR POWER DISTRIBUTION SYSTEM

FIELD OF THE INVENTION

The present invention relates to the field of electrical connection systems and more particularly to the distribution of electrical power in card cage assemblies.

BACKGROUND OF THE INVENTION

Card cages are known which comprise a framework within which a plurality of circuit panels or daughter cards are insertable, and within which is disposed a backplane transverse to the back edges of the daughter cards. The upper and lower daughter card edges conventionally are disposed within upper and lower channels defined by the card cage framework and extending to selected positions along the backplane to define the card position within the card cage and to guide the card during insertion into and removal from the card cage. Electrical circuitry of the cards is connected to electrical circuitry of the backplane by any of several types of known connectors and terminals, and is thereby interconnected by the backplane to circuitry of other cards of the array and to other electrical components on the opposite side of the backplane.

Typically each daughter card in present commercial card cages receives all necessary power for its components from the backplane through a plurality of terminals. One typical method involves providing a multilayer backplane having power-carrying circuit paths embedded within it, involving significant fabrication expense, to which terminals are engaged to transmit the power at current levels, ordinarily of about one ampere per terminal, through connectors to the daughter card. Connectors which must house the quite numerous power-carrying terminals also must house signal terminals for the primary purpose of providing signal transmission to and from the daughter cards; signal terminals are thus limited in number and in their position, which in turn limits the capabilities of the daughter cards. Also, the current levels presently available limit the number and types of components usable with the daughter cards.

One approach to distribute power to daughter cards in an improved manner is disclosed in U.S. Pat. No. 4,846,699 in which the power is provided to upper and/or lower edges of each daughter card rather than along the back edge. The upper and/or lower guide channels are defined by elongate electrical connectors containing a plurality of electrical terminals which are movable into and out of engagement with corresponding contact locations along the card by an actuation system within each connector. The plurality of terminals thus distributes electrical power to discrete locations and discrete power circuits on the card. Thus during card insertion and removal the contact sections of the terminals are retracted from the guide channel and would not engage any portions of the card nor interfere with insertion and removal of a card; only when the cards have been fully inserted and locked into position are the terminals moved into electrical engagement with the contact means along the card edge. Examples of such zero insertion force connectors are particularly disclosed in U.S. Pat. No. 4,789,352 and No. 4,834,665. With such connectors, conductors such as flat cables are needed to be routed through the card cage framework above and below the daughter cards and electrically connected to the terminals of the connectors and to a power supply for the card cage.

It is desired to provide a power distribution system for daughter cards of a card cage which utilizes a portion other than the back edge of each card for transmitting power to the card, without interfering with insertion or removal of the card.

It is desired to provide such a system which minimizes the amount of daughter card real estate utilized for receipt and return of power while retaining the benefits attained by a substantial plurality of power connecting sites.

It is additionally desired to provide a power distribution system which electrically connects with the card upon insertion and disconnects upon card withdrawal.

It is also desired to provide such a system which does not require a plurality of cables routed throughout the card cage.

It is further desired to provide such a system which would provide power to each card at substantially increased levels without significant voltage drop.

It is further desired that such a power distribution system not obstruct forced air flow between adjacent daughter cards in the card cage, needed for cooling.

SUMMARY OF THE INVENTION

The power distribution system of the present invention includes a pair of bus bars mounted to at least one of the upper and lower edges of a daughter card, with an insulator thereover. Each bus bar includes flange portions coextending inwardly along the corresponding card edge and includes a plurality of contact terminals secured to the bus bar and extending into plated through-holes into the card for electrical connection to power circuitry of the card. At the rearward ends of the bus bars are blade-shaped contact sections extending further rearwardly beyond the card's rear edge. Mounted to the framework at the rear of the card cage are upper and/or lower assemblies of pairs of receptacle contacts at each daughter card location and electrically connected to a power bussing system of the card cage having source and return paths, the receptacle contacts of each pair being associated with each bus bar of a daughter card to be inserted and matable with the blade-shaped contact section of the respective bus bar and comprising a separable interface. One of each pair of bus bars may be a source path and the other a return path, and preferably the blade-shaped contact section of the return path bus bar is longer to engage its respective receptacle contact first during card insertion and disengage last upon card withdrawal. The system is disclosed in U.S. patent application Ser. No. 07/546,335 filed Jun. 29, 1990 (AMP Case. No. 14832) filed assigned to the assignee herewith.

According to the present invention, the bus bars include elongate body sections having several flanges extending therefrom; the bus bars are of low resistance conductive metal and have a substantial mass because of their substantial current-carrying cross-section. The bus bars can be assembled together with insulation between their body sections, such that their flanges are laterally offset from the body sections and alternate with and are slightly spaced from each other along the bus bar length. Mounting of the bus bars to the card edge can be assuredly attained through the use of a plurality of compliant pin terminals which are firmly secured within holes through the bus bar flanges along the length of each bus bar and also firmly secured within corresponding through-holes along the card edge, and preferably are of the type having a pair of compliant sections as disclosed in U.S. Pat. No. 4,186,982. The compliant pin terminals also establish the substantial plurality of electrical connections to the card power-carrying circuitry along the card edge, for transmitting power to a substantial plurality of card sites considered necessary for effective power distribution. The bus bars may have several flange sections alternating with the flange sections of the other bus bar and having their card-proximate surfaces in a common plane to face a common surface of the card, and the compliant pin terminals may coextend in two rows into the card from a common side, facilitating assembly The compliant pin terminals being disposed in two spaced rows significantly resists damage to the card from torque resulting from lateral stress on the bus bars.

The present invention may be used with receptacle contacts such as of the type disclosed in U.S. Pat. No. 4,845,589 and include a receptacle contact section including a lead-in defining a capture range for matingly receiving thereinto a blade-shaped bus bar contact section, which has been substantially aligned therewith by guides of the card cage followed by rails of the daughter cards during card insertion. Each has a plurality of opposed spring arms of substantial spring strength establishing a contact normal force of about four pounds per spring arm, required to establish assured low resistance electrical connections for the transmission of power, for instance at 75 amperes.

Since the card edge connectors along the back edge of the card contain a substantial plurality of signal terminals small in size and closely spaced, it is crucial that the connectors which house them are precisely aligned with the mating connectors mounted to the backplane at least just before the signal terminals matingly engage. Alignment posts of the backplane connectors can enter post-receiving holes of the card edge connectors in order to incrementally adjust the position of the card edge connectors, provided that the power distribution system does not interfere with the incremental adjustment movement of the card's rear edge to conform the position of the card edge connectors to the backplane connector alignment posts. The effect of the substantial mechanical gripping of the blade-shaped sections by the receptacle contacts on the card edge adjustment, is minimized by mounting the receptacle contacts in a manner permitting floating thereof with little mechanical resistance of the type which would otherwise occur were the receptacle contacts to be rigidly mounted and the stiff spring arms to be even further deflected.

The receptacle contacts used with the present invention may be of the type disclosed in U.S. patent application Ser. No. 07/546,620 filed Jun. 29, 1990 and assigned to the assignee hereof. The receptacle contacts are loosely mounted along a shaft secured within a castellated clevis block permitting rotation therearound in a vertical plane parallel to a daughter card. Each receptacle contact is mounted in a loose fit between a respective pair of salients of the clevis block which combined with a loose fit with respect to the shaft permit float in two orthogonal dimensions to a limited extent sufficient to accommodate all adjustment movement of the card edge. Each receptacle contact may be assuredly connected to the power bussing system of the card cage by a corresponding rearward receptacle contact section gripping a respective blade-shaped section of the source or return card cage bussing means with substantial contact normal force, which provides the location about which the receptacle contact pivots when moved incrementally by the blade-shaped contact section of the source or return bus bar upon initial engagement during card insertion, and then incrementally by the card edge alignment system. Thus the assembly of receptacle contacts to the clevis block provides a floating separable interface, with the respective receptacle contacts permitted to move in two orthogonal directions (which define a plane parallel to the backplane) independently of each other while still gripping in the third or axial dimension the opposed blade-shaped contact sections of the card cage bussing system and the bus bars of the daughter cards. Thus the incremental adjustment movement essentially does not encounter resistance from needing to deflect the stiff spring arms of the receptacle contacts nor friction resistance from needing to move the blades along the arrays of opposed spring arms gripping them.

It is an objective of the present invention to provide a system for distributing electrical power to a substantial plurality of sites along the upper and/or lower edge of a daughter card, electrically connectable with bussing means of the card cage upon card insertion.

It is also an objective for the power connections of the system be matable and separable automatically during card insertion and withdrawal.

It is also an objective that such a power distribution system engage prior to signal connections being established between the daughter card and the backplane, and further that the return power circuit be established prior to the source power circuit.

It is additionally an objective that the two electrical connections already established during the intermediate stage of card insertion, each sufficient for transmitting 75 amperes, not interfere with the incremental adjustment in card edge position necessary at the final stage of daughter card insertion to precisely align the multitude of signal terminals in the high density card edge connectors with corresponding terminals of the back plane connectors.

It is a further objective that the bus bars of substantial mass be secured and electrically connected to a respective card edge in an assured manner and in a manner which minimizes the effects of torque on the card edge without necessitating mounting hardware nor heat, flux, solder nor adhesives in order to simplify card fabrication and assembly of the bus bars to the card edge.

It is an additional further objective that the bus bar assemblies for daughter cards be essentially independent of variations in card thickness in a large range of possible thicknesses, such as between 0.085 and 0.25 inches.

It is also a general objective that the power distribution system of the present invention minimize the voltage drop through all the electrical connections between the cage bussing system and the daughter card power circuits.

It is additionally an objective that the power distribution system and especially the bus bar assemblies not obstruct forced air flow between the daughter cards for cooling purposes.

An example of the preferred embodiment of the present invention will now be described with reference to the accompanying drawings.

BRIEF DESCRIPTION OF THE DRAWINGS

FIGS. 4A, 4B, and 4C are diagrammatic illustrations of an upper edge of a card module having a bus bar assembly mounted therealong, in several phases of insertion into a card cage and showing mating of the bus bar contact sections occurring prior to mating of the card and backplane connectors, with an alignment system shown;

FIGS. 5, 6 and 6A show a bus bar assembly for a card edge, prior to assembly and fully assembled to be mounted onto a card edge, with FIG. 6A being an enlarged view of a portion of a bus assembly showing an insulator retained over the bus bar pair;

FIG. 7 is an enlarged view of a flange of a bus bar with strips of compliant pin terminals to be mounted thereinto;

FIG. 8. is a representative section view of a portion of a card module edge having a bus bar assembly mounted therealong, showing several compliant pin terminals mechanically securing and electrically connecting the bus bar to the card;

FIG. 9 is an isometric view of a clevis block and representative receptacle contact therefore prior to assembly together, and showing the mounting shaft and a bushing;

FIG. 10 shows the receptacle contact block fully assembled and also showing the associated power bussing system of the card cage to which it will be connected upon mounting in the card cage;

FIGS. 11A to 11D diagrammatic illustrations in plan view of a bus bar assembly of a card module during a mating sequence, showing the floating nature of the receptacle contacts of the block of FIG. 10 in response to the first blade and the second blade in FIGS. 11A and 11B, the engagement of the alignment system of the card edge and backplane connectors in FIG. 11C, and the card fully inserted and fully connected in FIG. 11D.

DETAILED DESCRIPTION OF THE PREFERRED EMBODIMENT

Figure 1:
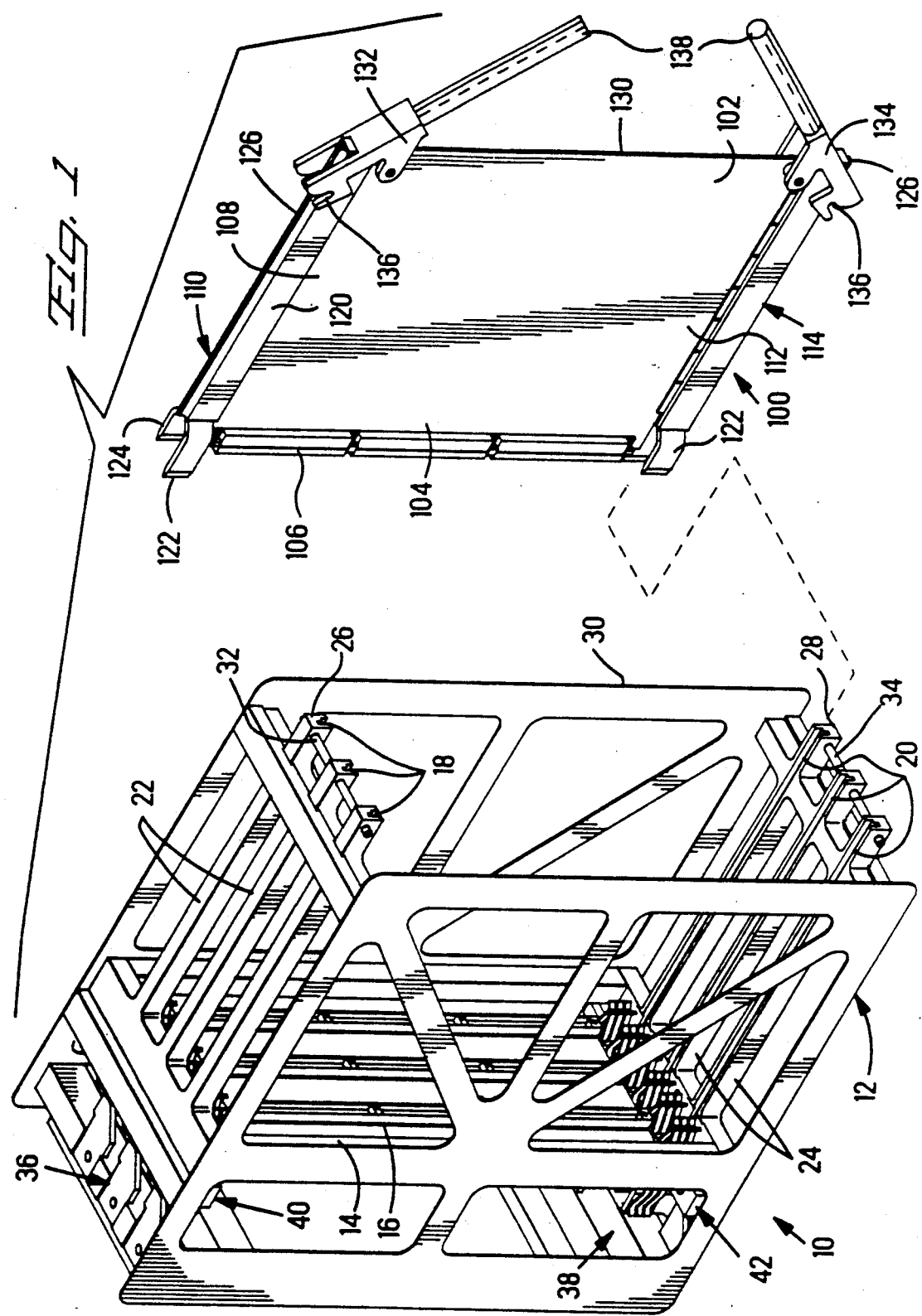
FIG. 1 is an isometric view of a card cage having a backplane and locations for a plurality of daughter cards, and a daughter card for insertion thereinto, having the power bussing system of the present invention.

The power distribution system with which the present invention is especially utile, is disclosed in U.S. patent application Ser. No. 07/546,335. A card cage 10 as in FIGS. 1 and 2 includes a framework 12, a backplane 14 on which are mounted a plurality of vertically disposed high density backplane connectors 16 corresponding to daughter card locations, and a plurality of pairs of upper and lower guide channels 18,20 defined in guide members 22,24 extending forwardly from backplane connectors 16 at the card locations to leading ends 26,28 at front face 30 of the cage 10. A representative daughter card module 100 includes a daughter card 102 having a rear edge 104 on which is mounted a single high density card edge connector 106 (or series of connectors). Along upper edge 108 of card module 100 of FIG. 1 is mounted a bus bar assembly 110, and along lower edge 112 is mounted a similar bus bar assembly 114. Each bus bar assembly includes a pair of first and second bus bars 116,118 (see FIGS. 5 and 6) covered by an insulator 120. At rearward ends of bus bar assemblies 110,114 are first and second blade-shaped contact sections 122,124 of the first and second bus bars 116,118 which extend outwardly from insulator 120 and rearwardly of rear card edge 104 and card edge connector 106.

Insulator 120 of each bus bar assembly 110,114 includes a rail 126 to follow guide channels 18,20 during card insertion. To assure that the card module is appropriately oriented, polarization may be provided by the depth of upper guide channel 18 being greater toward one side at 19 and the depth of lower guide channel 20 being greater toward the same side at 21; correspondingly the upper rail 126 would then include an offset narrow flange portion 128 toward that side after appropriate mounting and the offset narrow flange portion 128 of the lower rail would be positioned toward that same side after appropriate mounting so that the narrow rail flange portions 128 would prevent a daughter card module 100 being inserted in the improper inverted orientation wherein the rail flange portions would occur on the opposite side of the guide channels from the side of deeper channel portions 19,21. Other configurations of complementary rail/channel engagement geometries are possible, where the cross-section geometries of the upper and lower rail/channel systems are asymmetric between left and right sides to assure proper orientation of the daughter card during insertion; it is preferred that the geometries required of the upper and lower insulators (and likewise the upper and lower guide members) be mirror image opposites in cross-section so as to permit manufacture thereof by a common extrusion, and then be mountable in opposed orientations.

Card module 100 includes mounted pivotably along front edge 130 an insertion/ejection member 132 at the forward end of upper edge 108 and another such insertion/ejection member 134 at the forward end of lower edge 112, each of which includes a catch-receiving slot 136 cooperable with respective catches 32,34 of the card cage framework 12 to assist final stages of card module insertion. Insertion/ejection members 132,134 are mounted to daughter card 102 by pivot pins 144 extending through apertures of the card and through both tines of apertured clevises 146. Insertion/ejection members 132,134 are provided with elongate handles 138 movable flush to the daughter card forward edge 130; members 132,134 assist completion of card module insertion by providing mechanical advantage to overcome the resistance to bus bar and connector mating, and to retain the card module in position and also to initiate first stages of card module disengagement during withdrawal and removal. Catches 32,34 may be rods mounted transversely through leading ends of guide members 22,24. Also shown within the card cage 10 are upper and lower power bus assemblies 36,38, and forwardly thereof are receptacle contact blocks 40,42.

Figure 2:
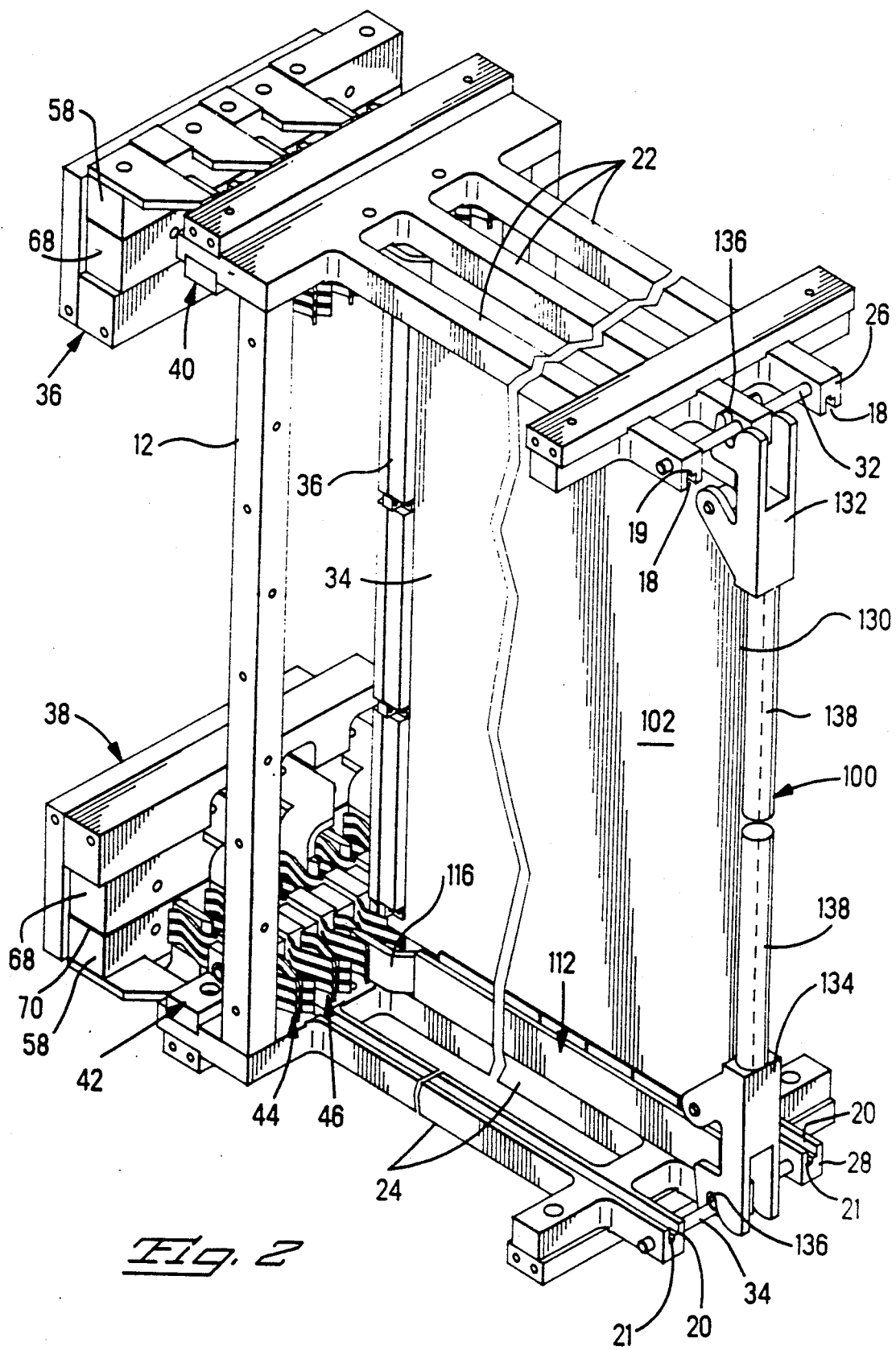
FIG. 2 is an isometric view of a card in position in its guide channels of the card cage of FIG. 1 showing the power distribution system.

FIG. 2 illustrates card module 100 in a fully inserted position within card cage 10, showing both bus bar assemblies 110,114 in mated engagement with respective pairs of receptacle contacts 44,46 of upper and lower receptacle contact blocks 40,42. Blade contact sections 116,118 have been received into receptacle contact sections 48,50 (FIG. 3) of receptacle contacts 44,46 each having a plurality of spring arms 52 opposed in pairs, the spring arms 52 having substantial spring strength. The backplane 14 of the card cage has been removed to show all of the essential portions of the separable interface of the power distribution system of the present invention from the bus bar assembly to the card cage bussing system.

Figure 3:
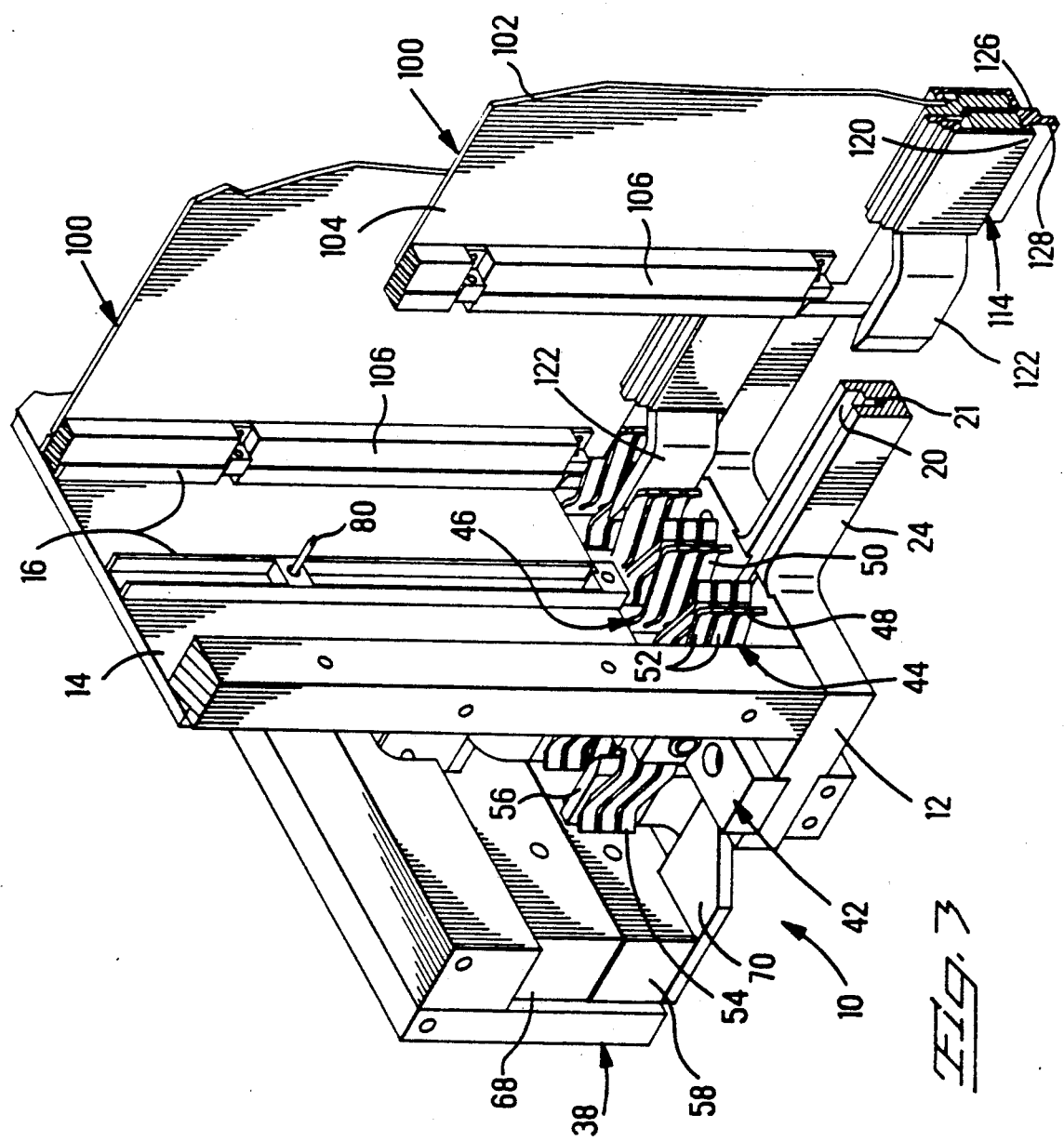
FIG. 3 is an enlarged portion of two card modules in the card cage of FIGS. 1 and 2 showing the separable interface of the power distribution system, with blade contact sections of the buses of a card module associated with float-mounted receptacle contact members of the card cage bussing system, and showing a card edge connector along the rear edge of a card module and an associated backplane connector.

In FIG. 3 is shown an enlargement of the lower separable power interface defined by the bus bar blade contact sections of lower bus bar assembly 114 and the receptacle contact sections 48,50 of contacts 44,46 mounted in lower block 42, with only blade contact section 122 of the return bus shown. The separable interface is mounted to framework 12 and disposed below the lower edge of backplane 14, and receptacle contact sections 48,50 extend forwardly of backplane 14 for early engagement with blade contact sections 122,124. Also shown is the rearward receptacle contact section 54 of a receptacle contact 44 mated with a blade-shaped contact section 56 of return bus member 58 of lower power bus assembly 38.

On backplane 14 is seen a lower portion of high density backplane connector 16 within which are secured a multitude of electrical signal contacts (not shown) which will mate with corresponding signal contacts (not shown) in card edge connector 106 mounted along rear edge 104 of daughter card 102. In order to assure that the plurality of mating signal contacts of the mating connectors will mate properly, an alignment system is provided comprising of for example several alignment posts 80 spaced along and solidly mounted to each backplane connector 16 and/or to backplane 14 and precisely located with respect to the signal contacts of the connector. The alignment posts 80 cooperate with post-receiving apertures (FIGS. 11A to 11D) of card edge connector 106 which apertures are similarly precisely located with respect to the card edge connector terminals. The engagement of the leading ends of alignment posts 80 with bearing surfaces of the aperture entrances (FIGS. 11C and 11D) urges the card edge connector (and the card module to which it is affixed) to adjust its position to be precisely aligned with the backplane connector, which could involve incremental movement vertically or horizontally or both as the card module 100 continues to be urged forwardly into card cage 10 along upper and lower guide channels 18,20.

Figure 4C:
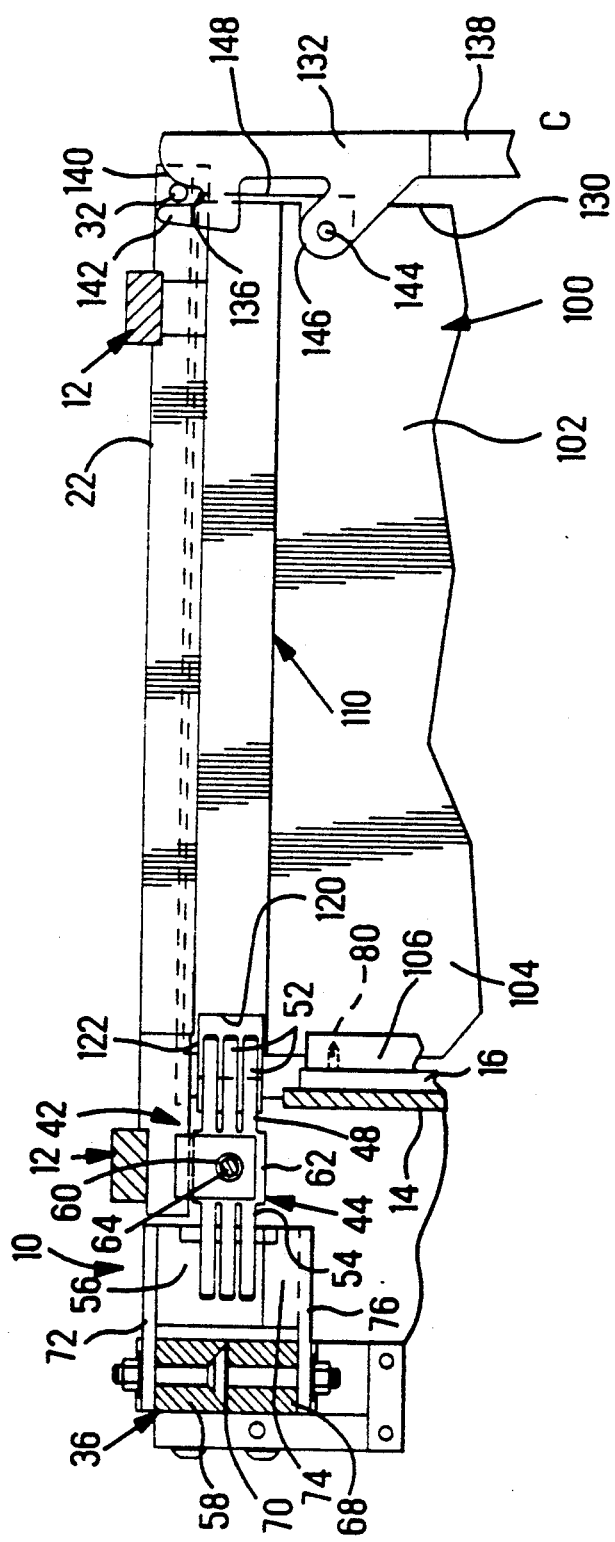

Referring now to FIGS. 4A to 4C, the mating sequence of card module 100 into card cage 10 is depicted in diagrammatic form and shows the upper bus bar assembly 110 mating with the upper separable interface comprised of upper receptacle contact assembly 42 and upper bus assembly 36 of the card cage. Receptacle contact member 44 is shown including an insulative bushing 60 extending through body section 62 and mounted on shaft 64 of clevis block 66 in upper contact assembly 42. Upper bus assembly 36 includes return bus member 58 and source bus member 68, with an appropriate insulation layer 70 therebetween; rearward receptacle contact section 54 of contact member 44 is mated onto blade-shaped contact section 56 depending from contact member 72 affixed to return bus member 58 and extending forwardly therefrom. Blade-shaped contact sections 74 similarly depend from contact members 76 affixed to source bus member 68 (FIG. 10) in each of upper and lower bus assemblies 36,38, arranged so that sections 74 extend upwardly to alternate with sections 56 extending downwardly to define a common row of blade-shaped contact sections for the array of rearward receptacle contact sections of contact assemblies 40,42.

In FIG. 4A card module 100 has been inserted most of the way into card cage 10 with rail 126 guided within guide channel 18 of guide member 22, and insertion/retention member 132 is oriented about pivot pin 144 into position A for catch 32 to abut arcuate engagement surface 140 forwardly of slot 136. Also seen is an insulative end cover member 148 similarly mounted by pivot pin 144 insulating the ends of the bus bars. Blade-shaped contact section 122 of the return bus bar extends rearwardly toward forward receptacle contact section 48 of contact member 44 to be received between opposed pairs of spring arms 52. Shorter blade-shaped contact section 124 of source bus bar is shown in phantom behind blade-shaped contact section 122. Card edge connector 106 on rear edge 104 of card 102 faces and is spaced from corresponding backplane connector 16 mounted on backplane 14, and one of the several alignment posts 80 for backplane connector 16 is shown extending forwardly theretowards.

In FIG. 4B insertion/ejection member 132 has been lowered to position B so that tine 142 opposed from arcuate engagement surface 140 is raised along the inside surface of catch 32 and bearing thereagainst, thus urging card module 100 further inwardly. The leading blade edge of blade-shaped contact section 122 has entered the lead-in defined by the diverging spring arm free ends of spring arms 52 of forward receptacle contact section 48 and has deflected the spring arms of the opposing pairs apart and entered therebetween meeting and overcoming substantial resistance to mating. Second, shorter blade-shaped contact section 124 will shortly thereafter similarly mate with corresponding forward receptacle contact section 50 again meeting and overcoming substantial resistance to mating, as insertion/ejection member 132 is moved further toward front card edge 130. Alignment post 80 approaches card edge connector 106 to begin its precision alignment function.

In FIG. 4C full card module insertion has been attained, with insertion/ejection member 132 in final position C along front card edge 130. The blade-shaped contact sections of both bus bars have been fully mated with respective receptacle contact sections. Alignment post 80 of backplane connector 16 has entered the corresponding aperture of card edge connector 106 and aligned the card edge connector with the backplane connector, and mating thereof has occurred with all pairs of mating terminals having been precisely aligned and mated.

Referring to FIGS. 5 to 8, the portions of bus bar assembly 110 for card module 100 are illustrated, and assembly thereof will now be described. Return bus bar 116 includes first blade-shaped contact section 122 extending therefrom, longer than second blade-shaped contact section 124 extending from source bus bar 118. Both contact sections 122,124 are offset a distance apart to mate with similarly spaced apart forward receptacle contact sections 48,50 of receptacle contact assembly 42 and include blade-like double beveled leading edges to facilitate mating therewith. Bus bars 116,118 are affixed together with a layer of insulative material 158 therebetween.

Bus bar 116 includes a plurality of flanges 150 alternating with recesses 152 and offset from the bus bar side surface toward bus bar 118 a distance equal to half a flange thickness plus half the thickness of insulative layer 158; bus bar 118 similarly includes a plurality of flanges 154 alternating with recesses 156 and offset toward bus bar 116. The flanges of each bus bar are located opposed from respective ones of the recesses of the other bus bar, and all flanges and recesses are shaped and dimensioned so that when the bus bars are affixed together with a layer of insulation 158 therebetween, the flanges of both define a common row specifically to define substantially a common plane of card-facing surfaces 160,162. Side edges of each flange are spaced from opposing side edges of adjacent flanges a precise amount for electrical isolation at spacings 164 which may be about 0.045 inches wide sufficient for voltage levels of the 5 to 10 volt range commonly desired in card cage power applications. The embodiment shown includes four flanges each about 1 inch long; however the number of flanges and their length can be modified as desired.

In FIG. 6A is shown one manner of retaining insulator 120 on a bus bar assembly: the flange-covering section 194 of the insulator is ultrasonically deformed at least one spacing 164 between flanges 150 and 154 so that a portion 196 of the insulator material is now embedded therebetween preventing axial insulator movement. Another manner of insulator securement optionally could comprise or include insulative member 148 (FIG. 4A) mounted to the daughter card at the front edge 130 at each insertion/ejection member 132,134 by the same pivot pin 144 by which the insertion/ejection member 132,134 is mounted. The corners of the insulator could be rounded if desired to facilitate forced air flow therearound.

In each flange 150,154 of both bus bars 116,118 are preferably two rows of pin-receiving apertures 166 to receive thereinto respective compliant sections 170 of first sections 172 of pin terminals 174. Pin terminals 174 are preferably stamped and formed on carrier strips 176 and retained thereon during assembly and thereafter. As seen in FIG. 8, carrier strips 176 extend integrally from central terminal sections 178 between first compliant sections 170 and second compliant sections 180 on second terminal sections 182. First compliant sections 172 are gripped within appropriately dimensioned apertures 166, thereby requiring at least about five pounds axial pushout force on each terminal for extraction. When bus bars 116,118 have each been fully loaded with compliant pin terminals 174, they are secured together so that second terminal sections 182 coextend outwardly from card-facing surfaces 160,162 of flanges 150,154.

Bus bar assembly 110 is applied to the reference surface side of card edge 108 by insertion of the plurality of second terminals sections 182 into respective through-holes 184 arrayed in two rows in each of alternating regions 186,188. Second compliant sections 180 are gripped by the wall surface of through-holes 184, thereby requiring at least about five pounds axial pushout force one each terminal for extraction. Compliant sections 172,182 are preferably of the type disclosed in U.S. Pat. No. 4,186,982 which can establish such substantial levels of force that assured mechanical and electrical connections are made by the terminals to the substrate without solder or any additional retention mechanism. Thus with a plurality for example of 92 terminals for each bus bar (23 per flange, in rows of 12 and 11 each) a total of 184 terminals having the specified type of compliant section is sufficient to establish that an aggregate force of at least about 900 pounds would be required to remove each of the bus bar assemblies 110,114. While such excellent retention force is defined by the particular compliant pin terminals disclosed, other mounting means such as bolts may be used for bus bar mounting if other types of terminals were to be used. Tooling and apparatus is in commercial use which can apply the necessary force of less than forty pounds per pin terminal, or in other words a maximum total of about 7500 pounds to apply each bus bar assembly to the daughter card.

In the embodiment shown, the carrier strips 176 define a selected spacing between the flanges and the card surface, and also serve to retain the terminals precisely spaced during assembly and to act as a stop mechanism to assure all pin terminals inserted to a common desired depth. The two-row array of terminals resists damage to the card edge from torque which may inadvertently be applied by the bus bar assembly; there is no one row of terminals which by itself would act to define a pivot point tending to permit rotation of the bus bar assembly about the row and thereby damage the card and the terminals; further the plurality of through-holes are now spaced farther apart than the same number would be spaced within a common row, allowing more card structure between the holes. Where the spacing of through-holes 184 cannot be positioned with absolute precision to correspond with the positioning of the terminals on a carrier strip, the compliant pin terminals may be separate from a carrier strip upon insertion.

The plurality of terminals extending from each flange to a respective through-hole region of the card edge define a plurality of distinct electrical connections therebetween dividing the current from the bus bar flange to a plurality of hole locations on the card, thus efficiently distributing the current to a substantial plurality of sites without exceeding the nominal capacity of individual terminals, and similarly efficiently gathering the return current. The carrier strips common the terminals after their receipt of the current by the first terminal sections of the row of terminals of the source bus bar (or by receipt from the second terminal sections of the return bus bar), and redistribute it to the second (or first) terminal sections, thus compensating for a single less-than-optimum electrical connection at one of the first or the second compliant sections of one of the terminals of a row. Distribution of Joule or resistive heating from the terminal/board interface is also assisted by the carrier strip conducting heat from individual terminals.

The card can be customized to transmit the current received by each through-hole to an embedded power plane which may intersect all through-holes of the region and then conduct the current elsewhere on the board to components such as representative integrated circuit devices 192 in FIG. 6. The compliant pin terminals and the mounting method disclosed accommodates different board thicknesses of from about 0.085 to 0.250 inches or more and is also forgiving of manufacturing tolerances in card thickness. Such essential independence from board thickness permits existing card cage systems having the power distribution of the present invention, to be upgraded without modification with new card modules having the bus bar assembly of the present invention, but having daughter cards of different thicknesses than the ones they replace.

The card may also utilize elevated bus bars of the type disclosed in U.S. Pat. No. 4,869,673 which will extend from the card edge to the interior regions of the card's major surfaces thus essentially freeing up the major surface for use by signal circuits and components only, and simplifying card fabrication by eliminating the need for multilayered construction for embedding power circuitry within the card. Appropriate electrical connections can be provided from the through-holes to contact sections of the elevated bus bars near the card edge by surface or embedded card circuitry; it is also possible to utilize compliant pin terminals to interconnect the bus bar flanges directly to tabs on the elevated bus bars, with other mounting means such as bolts provided to affix the bus bar assembly to the card edge.

Bus bars 116,118 can be extruded for example of low resistance copper alloy such as Alloy No. C110 and then flanges 150,154 formed from an initially continuous flange portion to define recesses 152,156; blade-shaped contact section 122,124 can then be formed, then annealed to half hard temper and thereafter plated with nickel underplating and then silver plating followed by application of a tarnish resistant coating. It may be desirable to extrude both bus bars from adjacent portions of the same copper alloy extrusion to best assure an identical thickness, which may be about 0.187 inches. Pin-receiving apertures 166 of appropriate diameter such as 0.040 inches can be machined into flanges 150,154; the spacing between apertures of a single row may be 0.100 inches, and the rows may be spaced 0.065 inches apart; the through-holes of daughter card 102 would be identically spaced within each region and have identical diameters of 0.040 inches after plating.

Compliant pin terminals 174 can be stamped from a continuous strip of stock copper alloy such as Alloy No. C260 and having generally a rectangular cross-section of 0.025 by 0.034 inches, but with the diagonal across each compliant section 170,180 of about 0.050 inches to assure the desired substantial gripping force upon being reduced during insertion into flange apertures 166 and through-holes 184 respectively from 0.050 to 0.040 inches. Insulator 120 may be extruded for example from a thermoplastic such as nylon and have a shape conforming snugly to the outer shape of the bus bars affixed together and also include a flange-covering section 194 as well as rail 126, with polarizing rail flange portions 128 easily extruded Insulator 120 may be inserted over the bus bar assembly before mounting to the card edge to facilitate handling of the bus bar assembly as a unit during card mounting, and then secured. Insulating layer 158 may be for example 0.005 inch double sided tape such as of MYLAR or KAPTON.

The components of receptacle contact assembly 40 (or 42) are shown in FIGS. 9 and 10, as disclosed in U.S. patent application Ser. No. 07/546,620. Each receptacle contact member 44 (or 46) includes a body section 62 having a hole 82 therethrough within which is secured an insulative bushing 60. A shaft-receiving hole 84 is formed through bushing 60 through which extends shaft 64. Clevis block 66 includes a plurality of salients 86 spaced therealong through each of which is a shaft-receiving aperture 88, and contact-receiving recesses 90 are defined between salients 86 and having controlled widths greater than the width of body sections 62 of contact members 44. Shaft 66 may be retained in the assembly by a pair of locking clips inserted on end sections extending from the clevis block and having annular recesses therearound; clevis block 66 preferably has mounting flanges 92 for being mounted to the card cage framework.

Each receptacle contact is preferably stamped from low resistance stock alloy such as Alloy No. C151 having a thickness of 0.062 inches for example, and then formed to have arrays of spring arms 52 in both forward and rearward receptacle sections 48,54, each spring arm having an angled free end The contact is then formed so that body section 62 is rectangular in cross-section and so that the spring arms of each contact section oppose each other a precise selected distance apart of for example about 0.120 inches at blade-engaging arcuate constrictions at the bases of now-diverging opposed angled free ends together now acting as a lead-in and defining a capture region for receipt of a slightly misaligned blade front end during mating. Since the forming of body section 62 involves abutting the free ends of the blank along a seam, the free ends must be locked together by a locking system such as the dovetail arrangement 78 wherein a tab is locked into an undercut groove similar to that disclosed in U.S. Pat. No. 4,932,906; the locking system assures that all opposed spring arms sustain equivalent and appropriate contact normal force upon deflection during mating with a corresponding blade. The entire contact member may be plated with nickel underplating and silver plating as desired for terminals conducting substantial current levels. Receptacle contact sections 48 and 54 are preferred to be similar to that disclosed in U.S. Pat. No. 4,845,589. Clevis block 66 may be molded for example of thermoplastic such as acetal resin, and shaft 64 may be a steel rod; insulative bushings 60 may be molded of thermoplastic such as nylon.

Receptacle contact assembly 42 is shown fully assembled in FIG. 10, in association with power bus assembly 38. Power bus assembly 38 includes source bus member 68 and return bus member 58 having insulation 70 therebetween. Contact members 72,76 may be formed from low resistance copper alloy like Alloy No. C110 about 0.187 inches thick, annealed to half hard temper if desired, and nickel underplated and silver plated and followed by application of a tarnish resistant coating. Contact members 72,76 are mounted to respective ones of bus members 58,68 so that blade-shaped contact sections 56,74 respectively alternate with each other opposed from respective rearward receptacle contact sections 54 of receptacle contact members 44,46 of assembly 42. Power bus members 58,68 may be extrusions of copper alloy such as Alloy C110 with flange-receiving recesses and mounting apertures formed thereinto in order to be secured such as by conventional hardware to an insulative support 94 such as of thermoplastic acetal or glass-filled polyester resin in order to be mounted to the framework of the card cage. Insulation 70 may be 0.03 inch thick glass-filled epoxy. Receptacle contact assembly 42 is also mounted to the card cage framework forwardly of the associated power bus assembly, with rearward contact sections 54 mated with appropriate associated ones of blade-shaped contact sections 56,74 under substantial contact normal force such as about four pounds per spring arm.

The incremental aligning capabilities of the mating of the bus bar assemblies 110,114 of card module 100 with the separable interface defined by receptacle contact assemblies 40,42 and also the critical after-mating adjustability thereof, will now be described with reference to FIGS. 11A to 11D, and with reference to FIGS. 4A to 4C. FIGS. 11A to 11D illustrate diagrammatically in plan view an upper bus bar assembly 110 of card module 100 approaching an upper contact assembly 40 mated with upper power bus assembly 36 of card cage 10, with a backplane connector 16 opposed from a corresponding card cage connector 106 on rear edge 104 of card 102 of card module 100; one of the several alignment posts 80 of backplane connector 16 is opposed from a corresponding post-receiving aperture 196 in card edge connector 106.

In FIG. 11A a lower guide member 24 of cage framework 12 is visible forwardly of backplane 14 and has a guide channel 20 approximately aligned with backplane connector 16 and alignment post 80 thereof. First blade-shaped contact section 122 of return bus bar 116 is opposing and is approximately aligned with a corresponding receptacle contact member 44, while second blade-shaped contact section 124 of source bus bar 118 is opposing and is approximately aligned with a corresponding receptacle contact member 46; the forward receptacle contact sections 48,50 thereof extend forward of backplane 14 above an upper edge thereof.

Receptacle contact members 44,46 are mounted to clevis block 66 on shaft 64 thereof Recesses 90 between salients 86 of clevis block 66 are slightly larger than the width of body sections 62 of members 44,46 permitting limited side-to-side movement and angular movement therebetween. Insulative bushings 60 through body sections 62 (FIG. 9) have shaft-receiving holes 84 with inside diameters slightly larger than the outer diameter of shaft 64, thereby permitting limited angular or skewing movement of each receptacle contact member as well as rotational movement about the shaft, all generally pivotable about the gripping engagement of rearward receptacle contact sections 54 onto blade-shaped contact sections 56,74 of power bus contact members 72,76. Thus receptacle contact assembly can be said to define a floating separable power interface while still firmly mechanically and electrically connected to contact members of the power bus assembly of the card cage, with forward receptacle contact sections possessing limited movement capability in any direction in a plane parallel to the backplane.

In FIG. 11B the front end of first blade-shaped contact section 122 has entered the lead-in of receptacle contact section 48 and has deflected apart the opposing spring arms 52 thereof, overcoming a peak insertion resistance of about eight pounds, while easily incrementally adjusting the position of the forward end of receptacle contact section 48 if necessary. Second blade-shaped contact section 124 is approaching receptacle contact section 50; card edge connector 106 is approaching backplane connector 16.

In FIG. 11C the front end of second blade-shaped contact section 124 has entered the lead-in of receptacle contact section 50 and has deflected apart the opposing spring arms 52 thereof, overcoming a peak insertion resistance of about eight pounds while easily incrementally adjusting the position of the forward end of receptacle contact section 50 if necessary, simultaneous with first blade-shaped contact section 122 being urged farther into receptacle contact section 48 against a friction resistance of about four pounds. Card edge connector 106 has been moved adjacent backplane connector 16, with the leading end 96 of alignment post 80 about to enter post-receiving aperture 196 at the entrance 198 defined by a chamfered lead-in.

In FIG. 11D leading end 96 of alignment post 80 has engaged the lead-in surfaces of aperture entrance 198 and has urged the card edge connector incrementally at least laterally (and commonly vertically as well), necessarily also urging the entire rear edge 104 of card module 100 simultaneously, as well as the bus bar assemblies 110,114. During the incremental adjustment movement, the blade-shaped contact sections 122,124 of both bus bar assemblies also must necessarily move; the floating separable interface defined by receptacle contact assemblies 40,42 are adapted to permit such movement of already-mated blades and receptacles with acceptably low mechanical resistance over and above simple inertia.

Therefore, incremental adjustment of the rear card edge 104 in the horizontal direction is accomplished without having to overcome the stiff spring arms of one side of each of the four receptacle contact sections 48,50 mated with the four blade-shaped bus contact sections 122,124. The aggregate mechanical resistance by the arrays of spring arms of the four receptacle contacts would have been up to about four pounds per mil for horizontal movement. With the present invention this stiffness (plus friction from blade/finger wiping during incremental pivoting) is reduced to about 0.01 pounds per mil. For example, where horizontal adjustment movement might require a horizontal translation of twenty mils, the total mechanical resistance would have been eighty pounds, whereas such horizontal translation in the present embodiment of the present invention would encounter a total mechanical resistance of about 0.20 pounds, plus a certain additional resistance due to friction as portions of the insulative bushings may bear somewhat against portions of the smaller-diameter shaft in the clevis block.

Adjustment movement is accomplished in the vertical direction without having to overcome the full friction resistance of the spring arms gripping the blades in order to move the blades relative to the spring arms. The aggregate friction resistance would have been up to about sixteen pounds for vertical movement; with the present embodiment of the present invention this aggregate friction resistance is reduced to about three pounds. Overcoming the deflection resistance of the spring arms and the friction resistance of the spring arms with respect to the blades would otherwise be necessitated were the receptacle contact members to be fixed mounted, and would have prohibitively stressed the precision alignment mechanism of the backplane and card edge connectors.

The power distribution system of the present invention permits powering of a daughter card module as a result of card insertion, where the power is brought to the side edges rather than the rear edge, thus freeing up all rear edge locations for signal connections with the backplane. Higher levels of power can be transmitted to the card than with commercially available systems. The system of the present invention distributes 75 amperes along one edge of the daughter card through 92 equi-current compliant pins with less than about 10 millivolts total voltage drop from the system bus to the most blade-remote daughter card site adjacent to the card edge bus. Return current is collected by the proximate bus with similar performance. Identical capability is provided by the card edge bus system affixed to the opposite edge of the daughter card. Where only one bus bar assembly is desired, an electrically inert or dummy rail member is applied to the opposite side edge in lieu of a bus bar assembly thereat.

The bus bar assembly of the present invention provides a pair of somewhat thin bus members opposing each other along facing major surfaces separated by a thin layer of insulation and providing a low impedance advantage along the daughter card edge. The thin nature of the bus members in the direction of the card array presents a relatively low profile module which permits forced air flow between adjacent cards from above and below the array. While the bus bars could be mounted to the card edge by conventional means such as bolts, the array of compliant pin terminals disclosed provide excellent mechanical mounting as well as excellent electrical connections at a substantial plurality of separate but closely spaced sites.

In the present invention, the bus assembly with its plurality of compliant pin terminals is assuredly but easily mounted to a card edge, and thus to real estate of the daughter card previously electrically unused. By compliant pin terminals entering the daughter card from a common side (the reference surface), the bus bars and the bus bar module are therefore essentially independent of substantial variations in card thickness. Since the card edge connectors along the rear edge are also mounted with respect to the same reference surface, and the rail of the insulator is positioned with respect to the reference surface, consequently the card cage adapted for the power distribution system of the present invention is also essentially independent of such card thickness variations, and can be standardized.

The sequence of power first, signal last is achieved without interfering with precision alignability of the signal connectors on the rear edge with the backplane connectors while the card is under power, and the return power circuit engages before the source power circuit. Precision alignability is attained by reason of float mounted power contacts of the card cage bussing system at each card location The present invention results in only minimal voltage drop from the card cage bussing system to the card's power circuitry.

Variations and modifications may be made to the preferred embodiment disclosed hereinabove, within the spirit of the invention and the scope of the claims.

What is claimed is:

1. A bussing means for a daughter card insertable into a card cage, for transmitting and distributing electrical power to the card from corresponding power bussing means of the card cage upon insertion of the card into the card cage at a selected location, comprising:

an assembly of a source bus member and a return bus member having elongated body sections secured together about insulative means therebetween, said assembly adapted and oriented to extend along at least a substantial portion of a card edge, each said bus member including at least one flange section depending from said body section thereof, at least one said flange section including a plurality of contact means corresponding to a like plurality of contact means of a daughter card along an edge thereof, each said bus member further including a contact means matable with a corresponding contact means of source and return ones of said corresponding power bussing means of said card cage upon insertion of said card into said card cage, and said bus members having an insulative covering thereover exposing at least said plurality of contact means for electrical engagement with said card contact means and exposing said contact means, defining a bus bar assembly to be mounted along at least one of an upper edge and a lower edge of a said daughter card.

2. A bussing means as set forth in claim 1 wherein each said flange section is adapted to extend a selected distance inward along a major surface of a said card from a said one of said upper edge and said lower edge thereof to extend over power circuit means of said card intersected by an array of through-holes, and each said flange section includes a corresponding array of pin terminals extending normally therefrom toward said array of through-holes, whereby said pin terminals are receivable into respective said through-holes to establish a plurality of electrical connections with said card power circuit means upon mounting of said bus bar assembly to said card.

3. A bussing means as set forth in claim 2 wherein said pin terminals are compliant pin terminals adapted to self-retain within said through-holes with substantial gripping force to resist withdrawal therefrom, whereby said compliant pin terminals define a means for mounting said bus members to said card.

4. A bussing means as set forth in claim 3 wherein said compliant pin terminals are disposed in at least a pair of rows.

5. A bussing means as set forth in claim 4 wherein said compliant pin terminals of each said row are fabricated on carrier strips and maintained thereon during assembly to respective said flange sections and during assembly of said bus bar assembly to a said card edge, thereby defining stop means for insertion of said compliant pin terminals into said apertures of said flange sections to a selected depth, and insertion of said compliant pin terminals into said through-holes to a second selected depth and thereafter commoning the pin terminals of each said row.

6. A bussing means as set forth in claim 2 wherein each said bus member includes a plurality of said flange sections of selected length alternating with flange-receiving recesses of lengths just larger than said selected length, and said flange sections of one said bus member are offset with said flange sections of the other said bus member to correspond with said flange-receiving recesses of said one bus member, whereby said bus members are securable together with said respective flange sections becoming interspaced between said flange sections of each other.

7. A bussing means as set forth in claim 6 wherein said flange sections are offset transversely with respect to the longitudinal axis of said bus member and toward the other said bus member during assembly a distance about equal to one-half the thickness of a said flange section, whereby upon said bus members being secured together said flange sections are disposed in a common aligned row such that card-facing surfaces thereof essentially define a common plane.

8. A bussing means as set forth in claim 6 wherein a small spacing is defined between facing edge surface of adjacent ones of said flange sections of said one and said other bus member, thereby electrically insulating said flange sections from each other.

9. A bussing means as set forth in claim 8 wherein said insulative covering has a constant cross-section therealong enabling fabrication thereof by extrusion, and said extruded insulative covering is securable about said bus members by deforming a portion thereof extending over card-remote surfaces of said flange sections into at least one said small spacing between adjacent ones of said flange sections, after insertion over said bus members from a common end thereof.

10. A bussing means as set forth in claim 1 wherein said insulative covering has a constant cross-section therealong enabling fabrication thereof by extrusion.

11. A bussing means as set forth in claim 10 wherein said insulative covering includes a rail for following a complementary guide channel of a guide means of said card cage during insertion of said card into said card cage.

12. A bussing means as set forth in claim 11 wherein said rail of said insulative covering further includes a portion therealong extending outwardly and being offset laterally from the median of said rail to define a polarizing means corresponding to complementary polarizing means of a corresponding said guide member of said card cage, whereby upon said bus bar assembly being mounted to said one of said upper and lower edges of a said daughter card, and said daughter card including rail means along the other of said upper and lower edges corresponding to an opposing said guide member, said offset rail portion requires proper orientation of a said card module prior to insertion into said card cage when said opposing guide member does not include a said complementary polarizing means diagonally opposed to that of said corresponding guide member, thereby defining a polarization means disallowing daughter card insertion in an inverted orientation into and between said corresponding guide member and said opposing guide member.

13. A bussing means as set forth in claim 11 wherein said rail has a particular cross-sectional shape selected to complement the cross-sectional shape of said guide channel of the particular one of said guide members into which said rail is to be inserted during appropriate card insertion into said card cage, said particular cross-sectional shape further selected not to complement an other cross-sectional shape of a said guide channel of an opposing one of said guide members associated with said daughter card, thereby defining a polarization means disallowing daughter card insertion in an inverted orientation into and between said particular guide member and said opposing guide member.

14. A bussing means as set forth in claim 1 wherein an insulative end cover is mountable to a said card along a forward edge thereof proximate said one of said upper edge and said lower edge, to include a portion coextending along an end of said bus bar assembly for insulation of end surfaces of said bus members.

* * * * *

UNITED STATES PATENT OFFICE
CERTIFICATE OF CORRECTION

Patent No. __5,030,108__  Dated __July 9, 1991__

Inventor(s) __David A. Babow et al.__

It is certified that error appears in the above-identified patent and that said Letters Patent is hereby corrected as shown below:

On the title page;

Please change the Serial Number from "548,133" to --546,133-- as per the filing receipt.

Signed and Sealed this

First Day of December, 1992

*Attest:*

DOUGLAS B. COMER

*Attesting Officer*     *Acting Commissioner of Patents and Trademarks*